(12) United States Patent
Drake

(10) Patent No.: US 6,778,267 B2
(45) Date of Patent: Aug. 17, 2004

(54) SYSTEMS AND METHODS FOR FORMING AN IMAGE OF A SPECIMEN AT AN OBLIQUE VIEWING ANGLE

(75) Inventor: Stephen John Drake, Manby (GB)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 09/961,695

(22) Filed: Sep. 24, 2001

(65) Prior Publication Data

US 2003/0058432 A1 Mar. 27, 2003

(51) Int. Cl.[7] .............................................. G01N 21/00
(52) U.S. Cl. ................................... 356/237.1; 356/601
(58) Field of Search ........................ 356/237.1–237.6, 356/601, 614, 394, 623, 450, 456, 458, 521, 326, 328, 305, 401

(56) References Cited

U.S. PATENT DOCUMENTS

| | | | |
|---|---|---|---|
| 4,255,032 A | * | 3/1981 | Matsumoto et al. ....... 350/3.85 |
| 4,391,524 A | | 7/1983 | Steigmeier et al. |
| 4,428,676 A | * | 1/1984 | Chastang et al. ........... 356/354 |
| 4,441,124 A | | 4/1984 | Heebner et al. |
| 4,614,427 A | | 9/1986 | Koizumi et al. |
| 4,746,186 A | | 5/1988 | Nicia |
| 4,877,326 A | | 10/1989 | Chadwick et al. |
| 4,889,998 A | | 12/1989 | Hayano et al. |
| 5,096,291 A | | 3/1992 | Scott |
| 5,218,423 A | | 6/1993 | Kishner |
| 5,317,380 A | | 5/1994 | Allemand |
| 5,495,331 A | * | 2/1996 | Wulf ............................. 356/328 |
| 5,633,721 A | * | 5/1997 | Mizutani ...................... 356/401 |
| 5,673,144 A | * | 9/1997 | Chastang et al. ............ 359/385 |
| 5,729,383 A | * | 3/1998 | Chastang et al. ............ 359/385 |
| 5,774,224 A | * | 6/1998 | Kerstens ...................... 356/394 |
| 5,917,588 A | | 6/1999 | Addiego |
| 6,020,957 A | | 2/2000 | Rosengaus et al. |
| 6,195,202 B1 | | 2/2001 | Kusunose |
| 6,288,786 B1 | * | 9/2001 | Rudd et al. .................. 356/623 |

OTHER PUBLICATIONS

International Search Report, PCT/US02/30242, mailed Feb. 14, 2003.

\* cited by examiner

*Primary Examiner*—Frank G. Font
*Assistant Examiner*—Sang H. Nguyen
(74) *Attorney, Agent, or Firm*—Ann Marie Mewherter; Conley Rose P.C.

(57) ABSTRACT

Systems and methods for forming an image of a specimen are provided. A system may include a relay lens configured to form an intermediate image of light scattered by a specimen. The relay lens may be positioned at an oblique viewing angle from an upper surface of the specimen. The system may also include a reflection grating positioned such that the intermediate image is imaged on the reflection grating. The reflection grating may be configured to reflect the intermediate image. The reflection grating may be positioned negative to the upper surface of the specimen, at the natural image plane. In addition, the system may include an objective lens configured to focus the reflected intermediate image. The system may further include an area detector configured to produce a signal representative of the focused image. An image of the specimen may be formed from the produced signal.

28 Claims, 2 Drawing Sheets

SYSTEMS AND METHODS FOR FORMING AN IMAGE OF A SPECIMEN AT AN OBLIQUE VIEWING ANGLE

BACKGROUND OF THE INVENTION

1. Field of the Invention

The present invention generally relates to systems and methods for forming an image of a specimen. Certain embodiments relate to systems and methods that include forming an image of a specimen at an oblique viewing angle.

2. Description of the Related Art

Fabricating semiconductor devices such as logic and memory devices may typically include processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes may include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor device fabrication process, defects such as particulate contamination and pattern defects may be introduced into the semiconductor devices. Such defects may be isolated to a single semiconductor device on a semiconductor wafer containing several hundred semiconductor devices. For example, isolated defects may be caused by random events such as an unexpected increase in particulate contamination in a manufacturing environment or an unexpected increase in contamination in process chemicals that may be used in fabrication of the semiconductor devices. Alternatively, the defects may be repeated in each semiconductor device formed across an entire semiconductor wafer. In an example, repeated defects may be systematically caused by contamination or defects on a reticle. A reticle, or a mask, may be disposed above a semiconductor wafer and may have substantially transparent regions and substantially opaque regions that are arranged in a pattern that may be transferred to a resist on the semiconductor wafer. Therefore, contamination or defects on a reticle may also be reproduced in the pattern transferred to the resist and may undesirably affect the features of each semiconductor device formed across an entire semiconductor wafer in subsequent processing.

Defects on semiconductor wafers may typically be monitored manually by visual inspection, particularly in the lithography process because many defects generated during a lithography process may be visible to the naked eye. Such defects may include macro defects that may be caused by faulty processes during this step. Defects that may be visible to the human eye typically have a lateral dimension greater than or equal to approximately 100 $\mu$m. Defects having a lateral dimension as small as approximately 10 $\mu$m, however, may also be visible on unpatterned regions of a semiconductor wafer. An example of a visual inspection method is illustrated in U.S. Pat. No. 5,096,291 to Scott and is incorporated by reference as if fully set forth herein. Prior to the commercial availability of automated defect inspection systems such as the systems illustrated in U.S. Pat. Nos. 5,917,588 to Addiego and 6,020,957 to Rosengaus et al., which are incorporated by reference as if fully set forth herein, manual inspection was common. Manual inspection id still widely used by lithography engineers.

Automated inspection systems were developed to decrease the time required to inspect a wafer surface. Such inspection systems may typically include two major components such as an illumination system and a collection-detection system. An illumination system may include a light source such as a laser that may produce a beam of light and an apparatus for focusing and scanning the beam of light. Defects present on the surface may scatter the incident light. A detection system may detect the scattered light and may convert the detected light into electrical signals that may be measured, counted, and displayed on an oscilloscope or other monitor. Examples of such inspection systems are illustrated in U.S. Pat. No. 4,391,524 to Steigmeier et al., U.S. Pat. No. 4,441,124 to Heebner et al., U.S. Pat. No. 4,614,427 to Koizumi et al., U.S. Pat. No. 4,889,998 to Hayano et al., and U.S. Pat. No. 5,317,380 to Allemand, all of which are incorporated by reference as if fully set forth herein.

SUMMARY OF THE INVENTION

An embodiment of the invention relates to a system configured to form an image of a specimen. The system may include a relay lens configured to form an intermediate image of light scattered by a specimen. As used herein, "light scattered" by a specimen may include any light returned from a specimen such as reflected, scattered, and/or diffracted by the specimen. The relay lens may be positioned at an oblique viewing angle from an upper surface of the specimen. The oblique viewing angle may be, for example, approximately 30 degrees as measured from grazing incidence. The relay lens may be a unit magnification symmetrical relay lens. The relay lens may also be substantially telecentric in object and image space. Alternatively, the relay lens may be substantially non-telecentric to increase keystone distortion of the image of the specimen. In this manner, a controlled amount of blur may be produced at the area detector.

The system may also include a reflection grating positioned such that the intermediate image is imaged on the reflection grating. As used herein, a "grating" may generally refer to an optical component that may have repeatable features, e.g., substantially parallel lines, intersecting lines, or concentric circles, formed upon a substrate that may reflect at least a portion of light striking the optical component. The reflection grating may be configured to reflect the intermediate image. The reflection grating may be positioned negative to the upper surface of the specimen, at the natural image plane. For example, if the oblique viewing angle is approximately 30 degrees as measured from grazing incidence, the reflection grating may be positioned at an angle of approximately −30 degrees to the optical axis of the relay lens. The reflection grating may be further positioned such that a grating surface of the reflection grating may be substantially perpendicular to the optical axis of an objective lens. The reflection grating may be substantially telecentric in object space.

The reflection grating may be a blazed reflection grating. A grating blaze angle of the reflection grating may be configured such that reflection of the intermediate image from each facet of the reflection grating may be substantially parallel to the optical axis of an objective lens. The reflection grating may include a grating pitch of approximately 10 lines per millimeter to approximately 30 lines per millimeter. Alternatively, the reflection grating may have a grating pitch configured to produce first order reflection of the intermediate image substantially parallel to the optical axis of the objective lens for a wavelength of the light.

In addition, the system may include an objective lens configured to focus the reflected intermediate image. The system may further include an area detector configured to produce a signal representative of the focused image. The area detector may include, for example, a time delay integration ("TDI") camera. An image of the specimen may be formed from the produced signal. The image may be a high resolution rectilinear image of a portion of the specimen. The image may also be used to detect defects on the specimen.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figures 1, 1A:
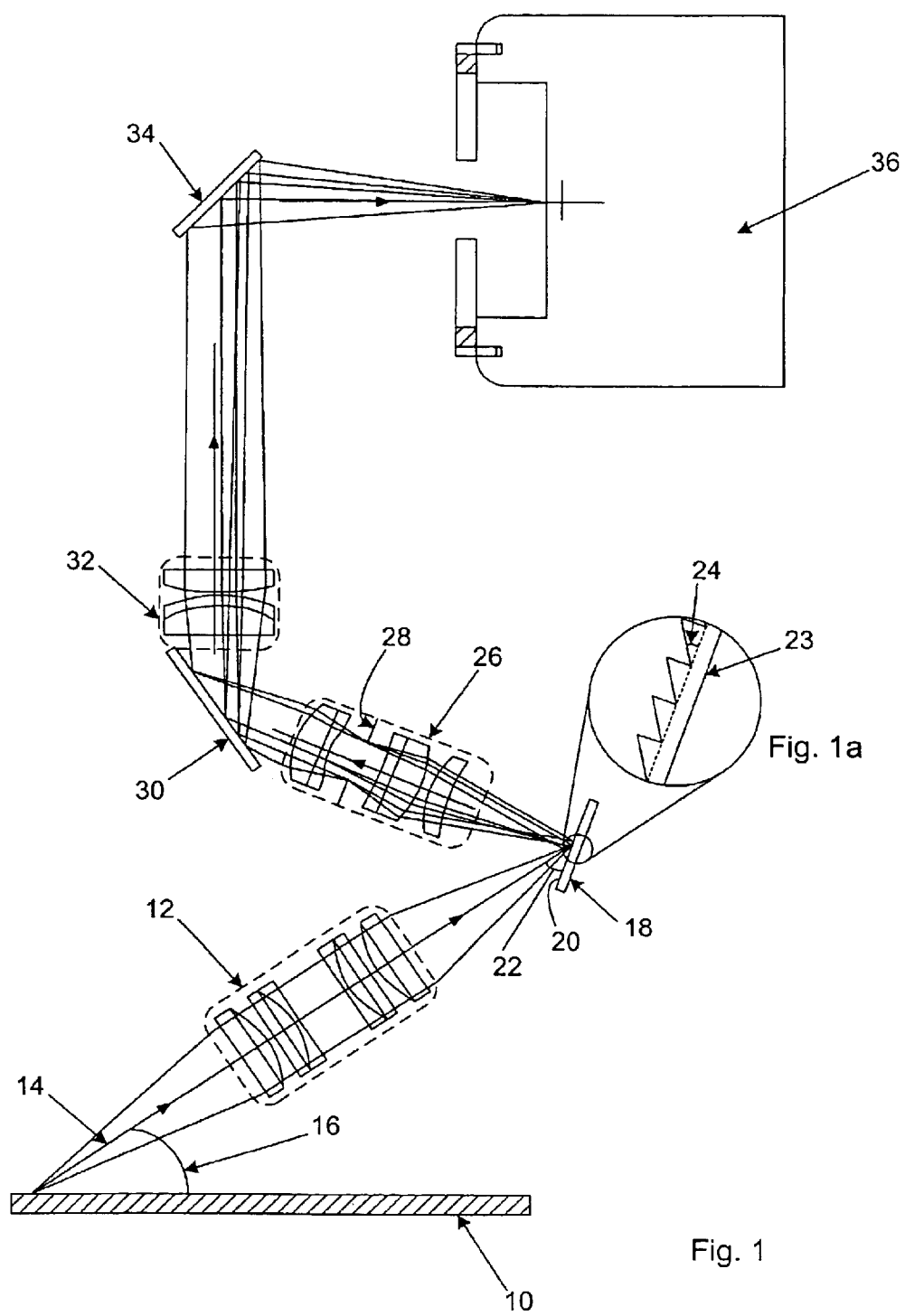
FIG. 1 depicts a schematic view of an embodiment of a system configured to form an image of a specimen.
FIG. 1a depicts an exploded cross-sectional view of an embodiment of a reflection grating.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description generally relates to systems and methods for forming an image of a specimen at an oblique viewing angle. Such an image may be commonly referred to as a dark field streak image. In addition, a system configured to form a dark field streak image may be configured in an arrangement commonly referred to as a dark field geometry. "Dark field" generally refers to a collection geometry configured to collect scattered light from an object. A system configured to form a dark field streak image may also be configured in a double dark field arrangement. "Double-dark field" generally refers to a collection geometry using steep angle oblique illumination and a collection angle outside of the plane of incidence. For example, such an arrangement may include a near-grazing illumination angle and a near-grazing collection angle to suppress surface scattering. This suppression occurs because of the dark fringe (also known as the Weiner fringe) near the surface that may occur due to interfering incident and reflected waves. In this manner, the term may be used to designate a system that may be configured for near-grazing incident illumination and near-grazing collection of scattered light.

The systems and methods described herein may provide high resolution rectilinear imagery, of a quality similar to imagery that may be obtained when viewing a specimen orthogonally, but at highly oblique viewing angles. In this manner, such a system may enable the effective use of area detectors such as cameras, which have appreciable dimension in the oblique viewing axis. Area detectors such as a TDI camera may make alignment of an illumination system less critical, may allow for a broader illumination line on a specimen, may reduce speckle in an image of a specimen, and may be less sensitive to the height of a specimen.

Such area detectors may not be used in a direct imaging system incorporating a low power objective. In such a direct imaging system, the detector may be tilted to compensate for viewing obliquity. An angle at which the detector may be tilted may vary depending on, for example, the objective magnification. For example, if a 4× objective is used at a viewing angle of approximately 30 degrees, as measured from grazing incidence, the detector may be positioned at approximately 8 degrees, as measured from grazing incidence. Such positioning of an area detector is not physically feasible. In addition, smaller compensation angles may provide negligible effect. Furthermore, tilting the detector may introduce keystone distortion into an image formed by the system. "Keystone distortion" generally refers to perspective distortion of an image in which sides of the image are bent either towards the center of the image or away from the center of the image. Therefore, although the image may be sharp, the image may be distorted.

Turning now to the drawings, FIG. 1 illustrates an embodiment of a system configured to form an image of specimen 10, which may be commonly referred to as a work piece. The specimen may include any specimen known in the art. For example, specimen 10 may include, but is not limited to, a wafer, a substrate, a semiconductor device, a reticle, a compact disc, and a disc platen. In addition, the specimen may include any specimen that may scatter, diffract, and/or reflect a detectable amount of light. The system may include an illumination system (not shown). The illumination system may include any illumination system known in the art. The illumination system may include, for example, a light source and any number of optical components such as lenses, mirrors, and filters. The illumination system may be arranged such that light generated by the light source may be directed toward a surface of specimen 10. Light directed toward the surface of specimen 10 may include monochromatic or broadband light. In addition, light directed toward the surface of specimen 10 may have a deep ultraviolet wavelength of about 248 nm, about 193 nm, or about 157 nm. Light directed toward the surface, however, may also have a wavelength in other ranges such as the visible or infrared wavelength range.

The system may include relay lens 12. Relay lens 12 may be configured to collect light 14 scattered from specimen 10. Light 14 scattered from specimen 10 may include light reflected, scattered, and/or diffracted from the specimen. In addition, relay lens 12 may be configured to form an intermediate image of light 14. Relay lens 12 may be positioned at oblique viewing angle 16 from an upper surface of specimen 10. Oblique viewing angle 16 may be, for example, approximately 30 degrees as measured from grazing incidence. The oblique viewing angle, however, may vary depending on, for example, characteristics of the specimen, configuration of the illumination system of the system, and configuration of the collection system. For example, the oblique viewing angle may range from approximately 5 degrees to approximately 70 degrees as measured from grazing incidence.

Relay lens 12 may be a unit magnification symmetrical relay lens. Alternatively, relay lens 12 may be configured to alter a magnification of the intermediate image. Relay lens 12 may also be substantially telecentric in object and image space. In this manner, principal rays of light from each object point and to each detector point may be substantially parallel to the optical axis of the relay lens. Therefore, relay lens 12 may have a substantially constant magnification with varying projection distances across the field of view. Alternatively, relay lens 12 may be substantially non-telecentric to increase keystone distortion of the image of the specimen. In this manner, a controlled amount of blur may be produced at the area detector. Such a controlled amount of blur may allow for a high collection numerical aperture and large detection pixel size without aliasing. "Aliasing" generally refers to distortion of an image in which one or more features of a specimen do not appear in an image of the specimen because a lateral dimension and a position of the features in the image correspond to a pixel spacing of the detector. A controlled amount of blur may increase a lateral dimension of such features in an image such that the lateral dimension is larger than the pixel spacing of the detector thereby reducing aliasing.

The system may also include reflection grating 18. Reflection grating 18 may be positioned such that an intermediate image formed by relay lens 12 may be imaged on the reflection grating. The reflection grating may be configured to reflect the intermediate image. Surface 20 of the reflection grating may be positioned negative to the upper surface of specimen 10, at the natural image plane. In this manner, angle 22 at which reflection grating 18 may be positioned with respect to the optical axis of the relay lens may be approximately equal and opposite to oblique viewing angle 16. For example, if oblique viewing angle 16 is approximately 30 degrees as measured from grazing incidence, reflection grating 18 may be positioned at angle 22 of approximately −30 degrees to the optical axis of the relay lens. The reflection grating may be further positioned such that grating surface 20 of the reflection grating may be substantially perpendicular to the optical axis of an objective lens. In this manner, the reflection grating may provide the required magnification to a detector. In addition, the reflection grating may be substantially telecentric in object space. As such, principal rays of light to each detector point may be substantially parallel to the optical axis of the reflection grating.

The reflection grating may be a blazed reflection grating. FIG. 1a illustrates an exploded cross-sectional view of an embodiment of reflection grating 18. As shown in FIG. 1a, reflection grating 18 may include substrate 23 in which grooves may be formed. The substrate may include a substantially transparent material such as, but not limited to, glass, plastic, a semiconductor material, and crystal. A layer of metal such as aluminum may be formed upon the substrate subsequent to formation of the grooves such that the grating may reflect light. In a blazed reflection grating, grooves formed in the substrate may have a regular geometric shape. For example, the grooves may form a regular geometric shape such as a sawtooth profile when viewed in cross-section, as shown in FIG. 1a. In this manner, most of the reflected light may be concentrated in one direction. Grating blaze angle 24 of the reflection grating may be configured such that reflection of the intermediate image from each facet of the reflection grating may be substantially parallel to the optical axis of an objective lens. In this manner, principal ray angles of light reflected from various points across the grating may be substantially equal. In addition, grating blaze angle 24 may be approximately equal to oblique viewing angle 16. For example, if oblique viewing angle 16 is approximately 30 degrees as measured from grazing incidence as described above, then grating blaze angle 24 may be approximately 30 degrees.

The reflection grating may have a grating pitch that may depend on configuration of the system. For example, a grating pitch of reflection grating 18 may be relatively coarse to obtain an appropriate depth of field across each facet of the reflection grating. In this manner, the reflection grating may have a grating pitch of approximately 10 lines per millimeter to approximately 30 lines per millimeter. For example, an appropriate grating pitch may be approximately 20 lines per millimeter. As such, the reflection grating may effectively be a Fresnel mirror. Alternatively, the reflection grating may have a grating pitch configured to produce first order reflection of the intermediate image substantially parallel to the optical axis of an objective lens for a wavelength of light 14. A grating pitch, which may produce first order reflection, may be determined by the equation: $P=L/\sin Q$, where P is the pitch separation of the grating lines, L is the wavelength of light used, and Q is the angle of incidence, as measured from an axis normal to the grating. For example purposes only, for laser light of wavelength 0.633 $\mu$m at an angle of incidence of approximately 60 degrees, a grating pitch of 0.73 $\mu$m or approximately 1368 lines per mm may produce first order reflection of the intermediate image. Appropriate reflection gratings are commercially available from, for example, Richardson Grating Laboratory, Rochester, N.Y.

In an alternative embodiment, a flat fine uniformly diffusing screen may replace the reflection grating in the system as described above. A diffusing screen may be configured to convert an approximately forward propagating beam of light into a more diffuse beam of light that may have a distribution of propagation angles relative to normal of the diffusing screen surface. In addition, a diffusing screen may be configured such that light emerging from the diffusing screen may have different angular distributions depending upon viewing angle requirements.

In addition, the system may include objective lens 26 configured to focus the reflected intermediate image. Objective lens 26 may include any objective lens known in the art such as a low power microscope objective. In addition, the objective lens may be configured to alter a magnification of the reflected intermediate image. For example, the objective lens may be configured to magnify the reflected intermediate image by approximately 4×. Objective lens 26 may include spatial filter 28. Spatial filter 28 may be positioned at the stop position within objective lens 26. Alternatively, a spatial filter may be positioned at the center of relay lens 12. In this manner, spatial filtering of light 14 may be effected at an aperture stop of a lens included in the system.

The system may also include folding mirror 30. Folding mirror 30 may be configured to direct light from objective lens 26 to tube lens 32. In addition, the system may include folding mirror 34. Folding mirror 34 may be configured to direct light from tube lens 32 to area detector 36. Folding mirror 30, tube lens 32, and folding mirror 34 may be configured as known in the art. Geometrical arrangement of folding mirror 30, tube lens 32, and folding mirror 34 may vary depending upon, for example, mechanical and/or spatial requirements or constraints of the system. In an alternative embodiment, folding mirror 30 and folding mirror 34 may be replaced with any optical component configured to alter a path of the focused intermediate image without substantially distorting the focused intermediate image. In addition, the system may include additional optical components such as, but not limited to, filters, dichroic mirrors, additional lenses, and additional folding mirrors.

Area detector 36 may be configured to produce a signal representative of the focused image. The area detector may include, for example, a time delay integration ("TDI") camera. An example of a TDI camera is illustrated in U.S. Pat. No. 4,877,326 to Chadwick et al., and is incorporated by reference as if fully set forth herein. An appropriate TDI camera may have a two-dimensional active area having lateral dimensions, for example, of approximately 26.6 mm by approximately 1.87 mm. The lateral dimensions of such a camera, having a pixel size of approximately 13 µm corresponds to an active area of approximately 2048 pixels by approximately 144 pixels. A TDI camera that may have an active area having different lateral dimensions, however, may also be included in the system. For example, lateral dimensions of the active area may vary depending upon, for example, characteristics of the illumination system and a magnification of the objective lens.

Alternatively, the area detector may include a charge-coupled device ("CCD") camera such as a ½ inch CCD camera. An appropriate CCD camera may have a two-dimensional imaging area having lateral dimensions, for example, of approximately 6.4 mm and approximately 4.8 mm. A CCD camera that has an imaging area having different lateral dimensions, however, may also be included in the system. The lateral dimensions of the imaging area may vary as described above. In addition, area detector 36 may include any detector known in the art that may be configured to produce a signal representative of a two-dimensional image of a specimen.

An image of the specimen may be formed from the signal produced by an area detector. For example, a signal produced by the area detector may be sent to an analog/digital converter (not shown). The analog/digital converter may be configured to send a digital signal representative of the signal produced by the area detector to a processing device (not shown) such as a computer. Alternatively, the area detector may be configured to send the produced signal directly to a processing device. The processing device may be configured to form an image of the specimen from the digital signal or, in the alternative, from the signal produced by the area detector. In addition, an image of the specimen may be formed using any device and any method known in the art.

The image may be a high resolution rectilinear image of a portion of the specimen. For example, the image may be viewed at a total magnification of about 4×, at about 30 degrees, as measured from grazing incidence, with an optical system of numerical aperture of about 0.15. In this manner, the image field size may be approximately 6.65 mm by approximately 47 mm. The minor dimension of the image may lie in the oblique axis of the system. A system, as described above, incorporating, for example, a reflection grating having a grating pitch of approximately 20 lines per mm may produce a streak image in which substantially the entire width of the streak image may be in focus with negligible distortion. In contrast, a direct imaging system incorporating a low power objective may produce a streak image in which only approximately 10% of the streak width (i.e., approximately 14 pixels) may be in focus.

Grating peaks of the reflection grating may be visible on the formed image as substantially parallel lines. Such parallel lines, however, may be relatively dark and may be substantially stationary. In contrast, detail of the formed image may be relatively bright and may move as light moves over the specimen. Such movement may be caused by, for example, an optical component of the system such as, but not limited to, an acousto-optical deflector ("AOD") or mechanical movement of a device upon which the specimen may be supported. Therefore, due to the differences between the substantially parallel lines formed by grating peaks and detail of the formed image, a signal produced by the grating peaks may be reduced, and even substantially eliminated, in the final image of the specimen. For example, an analog/digital converter may be configured to reduce, and to even substantially eliminate, signals produced by the grating peaks from the digital signal sent to the processing device. In addition, the processing device may include processing software operable to implement a method for reducing, and even substantially eliminating, images produced by the grating peaks from the formed image.

The image may also be used to detect defects on the specimen. For example, an image formed by the system may be used to detect particles and/or defects having vertical structure on a specimen. In addition, an image formed by the system may be used to detect other defects known in the art. Detecting defects on the specimen may include, but is not limited to, comparing the formed image to a reference image such as an image of a portion of a specimen substantially free of defects, comparing the formed image to an image of another portion of the specimen, an averaging method, or any other method known in the art.

The system may also be coupled to, or integrated into, a process tool. For example, the process tool may be a chemical-mechanical polishing tool, an etch tool, a lithography tool, a deposition tool, and an ion implantation tool. The process tool may also include any process tool configured to fabricate at least a portion of a semiconductor device. For example, each of the process tools described above may be used in combination to fabricate a complete semiconductor device. In this manner, the system may be used to form an image of a wafer prior to or subsequent to processing. In addition, the process tool may also include process tools configured to process other specimens as described above.

The system may be further coupled to a process chamber of a process tool. For example, in a lithography process tool, the system may be coupled to a coating chamber, a bake chamber, an exposure chamber, a developing chamber, or a chill chamber. In this manner, the system may be configured to form an image of a wafer prior to fabrication of at least the portion of a semiconductor device. For example, the system may be configured to form an image of the wafer after a robotic wafer handler of the process tool disposes the wafer in the process chamber. In addition, the system may be configured to form an image of a wafer subsequent to fabrication of at least the portion of a semiconductor device. In an example, the system may be configured to form an image of a wafer between steps of a process carried out in the process chamber or before a robotic wafer handler of the process tool removes the wafer from the process chamber.

An image formed by the system may be used to alter at least one parameter of an instrument coupled to a process tool. At least one parameter of an instrument of a process tool may be altered in response to the formed image using a feedback control technique, a feedforward control technique, and/or an in situ control technique. For example, an image of a specimen may be formed subsequent to a step of a process performed by the process tool. Depending on the image of the specimen formed by the system, a parameter of an instrument coupled to the process tool may be altered prior to processing of additional specimen using a feedback control technique. In addition, or alternatively, a parameter of an instrument coupled to the process tool may be altered prior to further processing of the specimen in response to the formed image. As such, the system may be used to reduce the propagation of defects in subsequent processing of additional specimens and/or of the specimen of which an image was formed.

Figure 2:
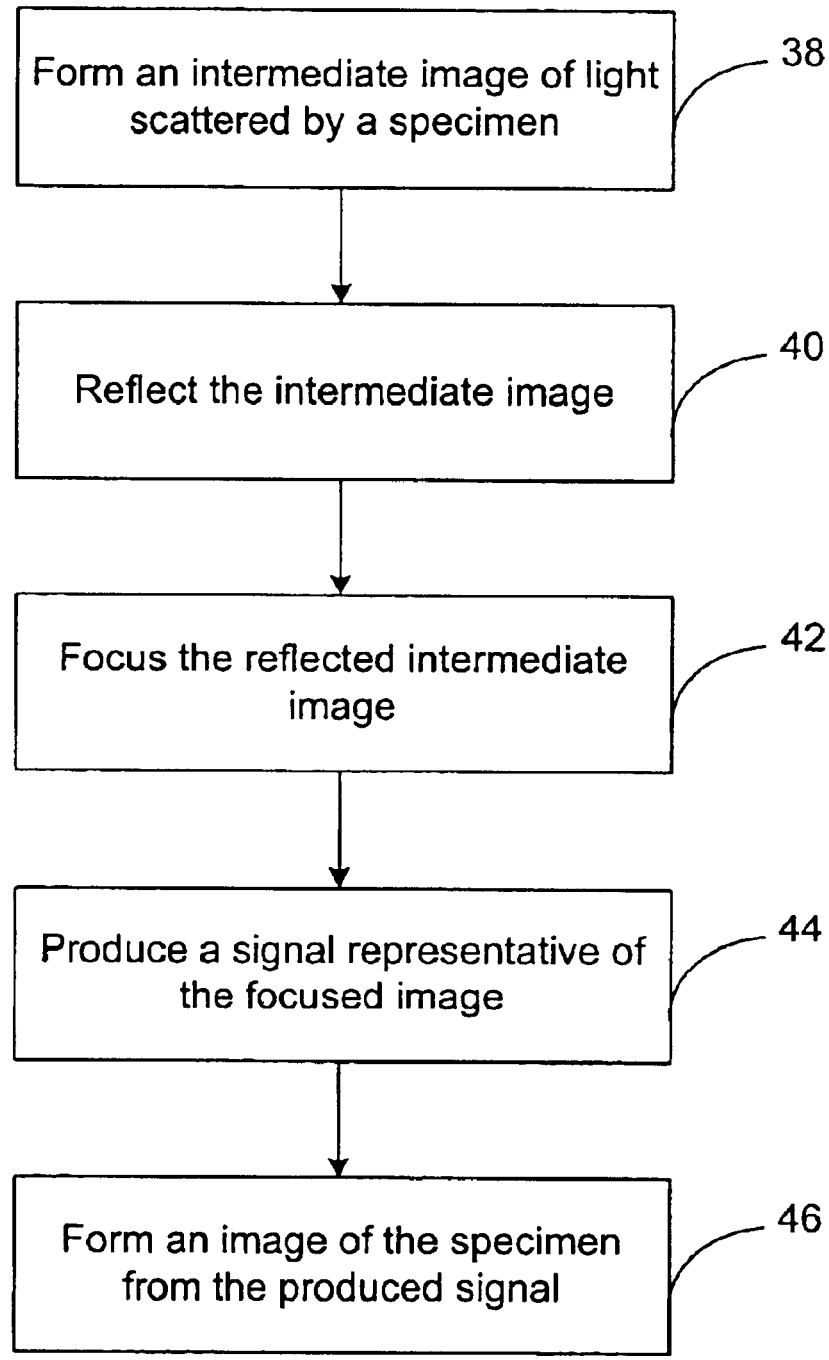
FIG. 2 depicts a flow chart illustrating an embodiment of a method for forming an image of a specimen.

An additional embodiment relates to a method for forming an image of a specimen, as shown in FIG. 2. The specimen may include any of the specimens described herein. The method may include forming an intermediate image of light scattered by the specimen, as shown in step 38. For example, an intermediate image of light scattered by the specimen may be formed with a relay lens positioned at an oblique angle from an upper surface of the specimen. The relay lens may be further positioned and configured as described herein. As shown in step 40, the method may also include reflecting the intermediate image. The intermediate image may be reflected with a reflection grating. The reflection grating may be positioned negative to the upper surface of the specimen, at the natural image plane. The reflection grating may be further positioned and configured as described herein. As shown in step 42, the method may include focusing the reflected intermediate image. For example, the reflected intermediate image may be focused with an objective lens, which may be configured as described herein. The method may further include producing a signal representative of the focused image, as shown step 44. The signal may be produced with an area detector, which may be configured as described herein. Furthermore, the method may include forming an image of the specimen from the produced signal, as shown in step 46. The image may include a high resolution rectilinear image of a portion of the specimen. In addition, the method may include detecting defects on the specimen using the formed image.

Further modifications and alternative embodiments of various aspects of the invention may be apparent to those skilled in the art in view of this description. For example, a system that may be configured to form an image of a specimen is provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to form an image of a specimen during use, comprising:
   a relay lens configured to form an intermediate image of light scattered by the specimen during use, wherein the relay lens is positioned at an oblique viewing angle from an upper surface of the specimen;
   a reflection grating positioned such that the intermediate image is imaged on the reflection grating, wherein the reflection grating is configured to reflect the intermediate image during use, and wherein the reflection grating is positioned negative to the upper surface of the specimen, at the natural image plane;
   an objective lens configured to focus the reflected intermediate image during use; and
   an area detector configured to produce a signal representative of the focused image, wherein an image of the specimen can be formed from the produced signal, wherein grating peaks of the reflection grating are visible on the image as substantially parallel lines, and wherein the substantially parallel lines are substantially stationary.

2. The system of claim 1, wherein the relay lens is substantially telecentric in object and image space.

3. The system of claim 1, wherein the relay lens is substantially non-telecentric to increase keystone distortion of the image of the specimen thereby producing a controlled amount of blur at the area detector.

4. The system of claim 1, wherein the relay lens comprises a unit magnification symmetrical relay lens.

5. The system of claim 1, wherein the oblique viewing angle comprises approximately 30 degrees as measured from grazing incidence, and wherein the reflection grating is further positioned at an angle of approximately −30 degrees to the optical axis of the relay lens.

6. The system of claim 1, wherein the reflection grating comprises a blazed reflection grating.

7. The system of claim 1, wherein the reflection grating is further positioned such that a grating surface of the reflection grating is substantially perpendicular to the optical axis of the objective lens.

8. The system of claim 1, wherein a grating blaze angle of the reflection grating is configured such that reflection of the intermediate image from each facet of the reflection grating is substantially parallel to the optical axis of the objective lens.

9. The system of claim 1, wherein the reflection grating is substantially telecentric in object space.

10. The system of claim 1, wherein the reflection grating comprises a grating pitch of approximately 10 lines per millimeter to approximately 30 lines per millimeter.

11. The system of claim 1, wherein the reflection grating comprises a grating pitch configured to produce first order reflection of the intermediate image substantially parallel to the optical axis of the objective lens for a wavelength of the light.

12. The system of claim 1, wherein the image can be used to detect defects on the specimen.

13. The system of claim 1, wherein the area detector comprises a time delay integration camera.

14. The system of claim 1, wherein the image comprises a high resolution rectilinear image of a portion of the specimen.

15. A method for forming an image of a specimen, comprising:
   forming an intermediate image of light scattered by the specimen with a relay lens positioned at an oblique viewing angle from an upper surface of the specimen;
   reflecting the intermediate image with a reflection grating positioned negative to the upper surface of the specimen, at the natural image plane;
   focusing the reflected intermediate image;
   producing a signal representative of the focused image with an area detector; and
   forming the image of the specimen from the produced signal, wherein grating peaks of the reflection grating are visible on the image as substantially parallel lines, and wherein the substantially parallel lines are substantially stationary.

16. The method of claim 15, wherein the relay lens is substantially telecentric in object and image space.

17. The method of claim 15, wherein the relay lens is substantially non-telecentric, the method further comprising increasing keystone distortion of the image of the specimen to produce a controlled amount of blur at the area detector.

18. The method of claim 15, wherein the relay lens comprises a unit magnification symmetrical relay lens.

19. The method of claim 15, wherein the oblique viewing angle comprises approximately 30 degrees as measured from grazing incidence, and wherein the reflection grating is further positioned at an angle of approximately −30 degrees to the optical axis of the relay lens.

20. The method of claim 15, wherein the reflection grating comprises a blazed reflection grating.

21. The method of claim 15, wherein focusing the reflected intermediate image comprises focusing the reflected intermediate image with an objective lens, and wherein the reflection grating is further positioned such that a grating surface of the reflection grating is substantially perpendicular to the optical axis of the objective lens.

22. The method of claim 15, wherein focusing the reflected intermediate image comprises focusing the reflected intermediate image with an objective lens, and wherein reflecting the intermediate image comprises reflecting the intermediate image from each facet of the reflection grating substantially parallel to the optical axis of the objective lens.

23. The method of claim 15, wherein the reflection grating is substantially telecentric in object space.

24. The method of claim 15, wherein the reflection grating comprises a grating pitch of approximately 10 lines per millimeter to approximately 30 lines per millimeter.

25. The method of claim 15, wherein focusing the reflected intermediate image comprises focusing the reflected intermediate image with an objective lens, and wherein reflecting the intermediate image comprises producing first order reflection of the intermediate image substantially parallel to the optical axis of the objective lens for a wavelength of the light.

26. The method of claim 15, further comprising detecting defects on the specimen using the formed image.

27. The method of claim 15, wherein the area detector comprises a time delay integration camera.

28. The method of claim 15, wherein the image comprises a high resolution rectilinear image of a portion of the specimen.

* * * * *